United States Patent [19]

O'Rourke et al.

[11] Patent Number: 5,039,224

[45] Date of Patent: Aug. 13, 1991

[54] SELF-REFERENCING REMOTE OPTICAL PROBE

[76] Inventors: Patrick E. O'Rourke, 157 Greenwood Dr., Martinez, Ga. 30907; William S. Prather, 2419 Dickey Rd., Augusta, Ga. 30906; Ronald R. Livingston, 137 Breckenridge Dr., N. Augusta, Ga.

[21] Appl. No.: 478,327

[22] Filed: Feb. 12, 1990

[51] Int. Cl.⁵ .................. G01N 21/05; G01N 21/85
[52] U.S. Cl. .................................. 356/434; 356/436; 356/440
[58] Field of Search .............. 356/434, 244, 246, 411, 356/432, 440, 436

[56] References Cited

U.S. PATENT DOCUMENTS

| | | | |
|---|---|---|---|
| 2,912,895 | 11/1959 | Hamilton | 356/413 |
| 3,572,952 | 3/1971 | Anthon | 356/246 |
| 3,707,331 | 12/1972 | George et al. | 356/246 |
| 3,802,786 | 4/1974 | Anderson et al. | 356/246 |
| 3,817,627 | 6/1974 | Fletcher | 356/180 |
| 3,841,765 | 10/1974 | Lambert et al. | 356/246 |
| 4,447,546 | 5/1984 | Hirschfield | 356/445 |
| 4,451,152 | 5/1984 | Topol et al. | 356/440 |
| 4,519,710 | 5/1985 | Luce et al. | 356/411 |
| 4,715,710 | 12/1987 | Andersen | 356/246 |
| 4,762,798 | 8/1988 | Deutsch | 436/67 |

*Primary Examiner*—Vincent P. McGraw
*Assistant Examiner*—La Charles P. Keesee
*Attorney, Agent, or Firm*—Harold M. Dixon; Stephen D. Hamel; William R. Moser

[57] ABSTRACT

A probe for remote spectrometric measurements of fluid samples having a hollow probe body with a sliding reflective plug therein and a lens at one end, ports for admitting and expelling the fluid sample and a means for moving the reflector so that reference measurement can be made with the reflector in a first position near the lens and a sample measurement can be made with the reflector away from the lens and the fluid sample between the reflector and the lens. Comparison of the two measurements will yield the composition of the fluid sample. The probe is preferably used for remote measurements and light is carried to and from the probe via fiber optic cables.

19 Claims, 1 Drawing Sheet

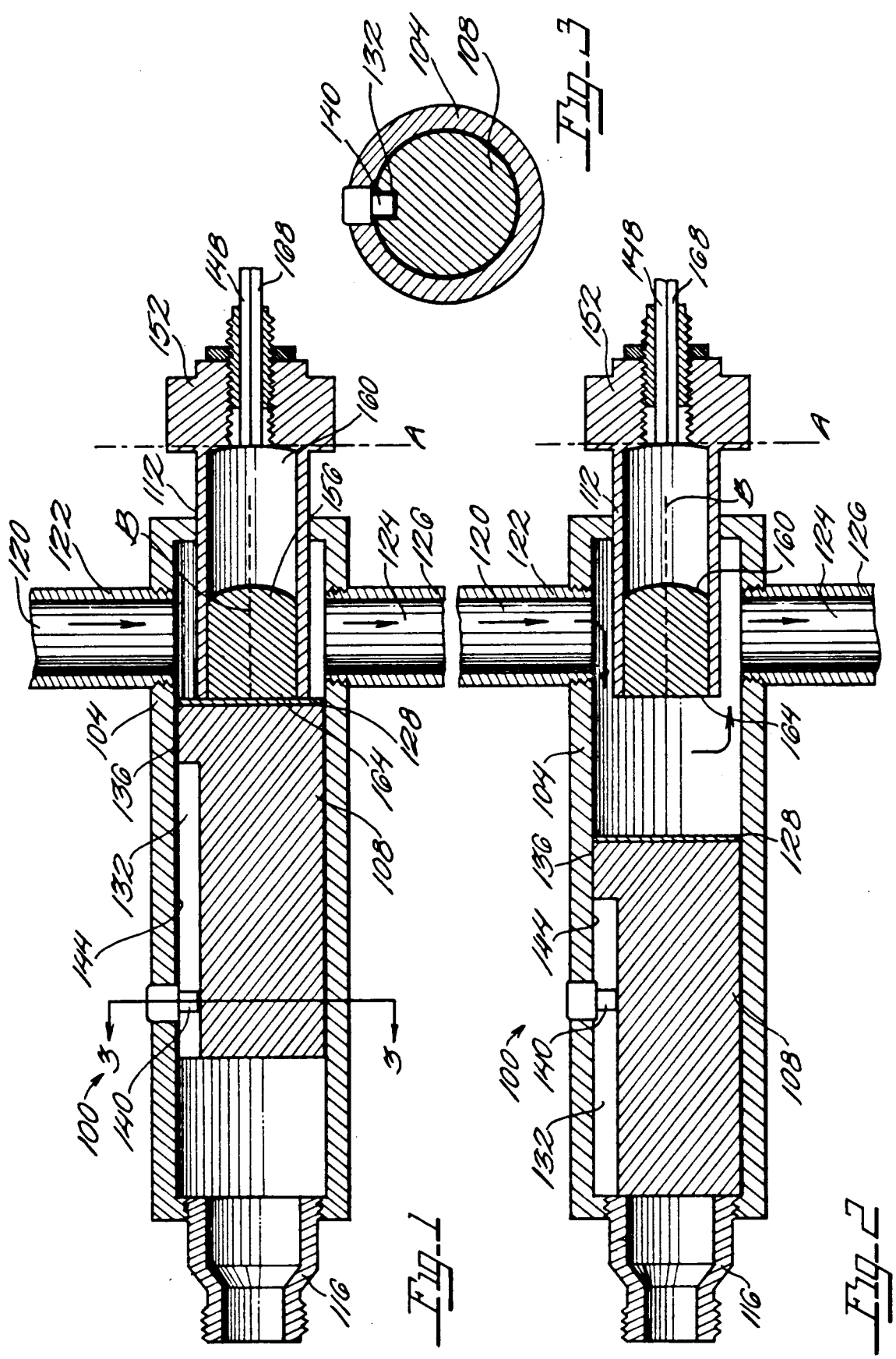

SELF-REFERENCING REMOTE OPTICAL PROBE

The U.S. Government has rights in this invention pursuant to Contract No. DE-AC09-76SR00001 between the U.S. Department of Energy and E. I. DuPont de Nemours & Co.

BACKGROUND OF THE INVENTION

Field of the Invention and Contract Statement

The present invention relates to the devices for spectrometric measurements of a fluid or gas sample. More particularly, it relates to an apparatus and method for making reference and sample spectrometric measurements remotely nearly simultaneously.

DISCUSSION OF BACKGROUND

The freqeuncy distribution, or spectrum, of the light absorbed by a substance can be used to identify its composition, and the amount of light absorbed at different frequencies depends on the concentration of each component of the substance. The absorption spectrum is characteristic not only of the substance sampled but of the light source and the apparatus used for the measurement, particularly the sample container and any media through which the light beam passes. The absorption spectrum of the sample can be found by discounting that part of the measured spectrum which is due to factors other than the sample itself. This is typically done by comparing the test measurement, made with the sample present, with a reference measurement made with the same apparatus but without the sample. If absorption measurements are made in the appropriate wavelength range, the chemical composition of the sample as well as the concentration of its constituents can be identified.

A typical spectrophotometer measurement system includes three basic elements: a light source, a sample cell, and a detector. Light from the source passes through the sample cell, then is focused onto a detector. The absorbance of the sample at each frequency is a function of the detector output signal. The absorbance is defined as:

$$A(v) = -\log_{10}(Tv),$$

where $$T(v) = I(v)/I_0(v),$$

I is the transmitted light intensity, $I_0$ the incident light intensity and v denotes the frequency of the light source.

Absorption spectra can can be measured for solids, gases, or substances in solution. Sample cells may be made of glass for measurements in the visible or near ultraviolet regions (down to about 350 nm), or made of silica for shorter wavelengths. The optical path length of the container is usually on the order of 10 mm, but can range from about 1 mm to 100 mm, depending on the system being measured. The solvent must be optically transparent in the region of frequencies of interest; common solvents include ethanol, benzene, acetone, and water. A solid sample is typically deposited on an optically-flat transparent plate, either directly or by evaporation from solution. The absorption spectrum of a solid sample can also be measure by diffuse reflectance off its surface instead of transmission.

A simple spectrometric analyzer system has one light source, one sample cell, and one detector. A light beam is passed through the sample container, and its absorption spectrum is measured by the detector. The spectrum is compared with those of other samples containing known concentrations of various substances in order to determine the quantitative amounts of these substances present in the test sample. The analyzer must be calibrated periodically by measuring the spectrum of a sample with known properties and making any adjustments needed to standardize the output of the detector. The accuracy of the measurement depends on precise positioning of the lenses, steady production of light from a stable source, exact spacing between the light source and detectors, similarity of the test and reference sample containers, and other such factors. This type of analyzer system has no compensation for drift due to environmental factors such as temperature, or error due to contamination of the optical surface or differences in the sample containers.

In a dual-beam analyzer system, the light beam from a single source is split into two separate beams, with one being directed through the test sample and the other through a reference sample. The two beams are focused alternately onto a single detector, which is used to measure the absorption spectra of the light transmitted through both samples. The spectrum of the test sample can thus be compared to a reference spectrum taken at the same time under the same conditions. However, the absorption properties of the test and reference containers may differ slightly, which may affect the accuracy of the results. Another type of dual-beam system may include two detectors, one for the test sample and one for the reference sample. Such a system has the added disadvantage of using two detectors which may yield slightly dissimilar results. Measurements taken over an extended period of time could also be suspect due to contamination of the optical surfaces of the system.

In addition, although spectrophotometry is an accurate and precise technique for identifying the composition of a sample under laboratory conditions, it has heretofore been less practical for use outside the laboratory. Obtaining the appropriate reference measurements under certain circumstances can be difficult or impossible. It may be impossible to remove a chemical substance from its environment or to control the source or souces of light.

A better system for on-line measurement of absorption spectra would include a means for remotely recording the data from test and reference samples with the same instruments and the same sample cell. Recoding the data at nearly the same time would reduce error caused by environmental factors and drift would be small. In particular, any contamination of the optical surfaces of the system would affect the two measurements equally, but not affect the comparison between the two: it is the difference between the test and reference samples which is of interest.

SUMMARY OF THE INVENTION

An object of the invention is to provide a probe for use in making optical absorption measurements.

Another object of the invention is to provide a probe for remote optical absorption measurements of the composition of fluid and gas samples.

To achieve the foregoing and other objects and in accordance with the purpose of the invention, as embodied and broadly described herein, the invention comprises a probe for optical absorption measurements of fluid and gas samples. The probe has a sliding reflecting plug inside, a lens at one end, ports for admitting and expelling the fluid sample, and a means for moving the plug toward and away from the lens. Light is carried to the probe from a light source and away from the probe to a spectral detector via fiber optic cables. To make a measurement, the fluid sample is admitted to the interior of the probe between the plug and the lens, light from the light source is carried by one fiber optic cable to the probe, focused by the lens on the reflective plug through the sample so that the light is reflected back to the lens and carried by the second fiber optic cable to a detector for analysis. To reference the sample measurement, the plug is slid toward the lens, thereby expelling most of the fluid sample between the lens and the reflecting plug so that, when the light is transmitted, it passes through very little of the fluid sample.

The probe can be positioned for remote spectrophotometric or colorimetric measurements taken over an extended period of time in groundwater, well water, process streams or in other remote environments thereby eliminating substantial labor costs and time in sample gathering and the inaccuracies introduced by such sample gathering and delays.

The probe's simplified design and operation lends itself to automated data gathering.

Reference is now made in detail to the present preferred embodiment of the invention, an example of which is given in the accompanying drawings.

A BRIEF DESCRIPTION OF THE DRAWINGS

The accompanying drawings, which are incorporated in and form a part of the specification, illustrate the invention and, together with the description, serve to explaining the principles of the invention. In the drawings:

FIG. 1 shows a side, cross sectional view of a probe in the reference position according to a preferred embodiment;

FIG. 2 shows a side, cross sectional view of the probe in the sample measuring position acording to a preferred embodiment; and FIG. 3 shows an end, cross sectional view of the probe along lines 3—3 FIG. 1.

DETAILED DESCRIPTION OF THE INVENTION

The present invention is a device and method for obtaining self-referenced, remote optical absorption measurements of fluid samples for spectrometric analysis.

FIG. 1 shows a side, cross sectional view of a probe 100 according to a preferred embodiment of the present invention. Probe 100 comprises probe body 104, a slidable plug 108 inside probe body 104, a lens assembly 112 at one end of probe body 104, a bottom port 116 at the opposing end of probe body 104, an inlet 120 defined by inlet port 122 and an exit 124 defined by exit port 126 in the sides of probe body 104. A sample of the fluid, which can be either a liquid or a gas, enters inlet 120 and exits at exit 124.

Reflecting plug 108 fits closely within probe body 104 and is dimensioned so as to slide freely within probe body 104 along the long axis of probe 100. Plug 108 has its reflecting end 128 facing lens assembly 112. Reflecting end 128 is perpendicular to the long axis of probe 100 and plug 108. Guiding plug 108 is a longitudinal groove 132 on the exterior surface 136 of plug 108 and a pin 140 on interior surface 144 of probe body 104. Pin 140 rides in groove 132 to guide plug 108 as it moves toward and away from lens assembly 112.

It is clear that, alternatively, a groove could be in interior surface 144 and a pin on exterior surface 136. It is important that plug 108 be able to move toward and away from lens assembly 112 without rotation about its long axis.

Light from a light source (not shown) is carried by a first fiber optic cable 148 to lens assembly 112. Lens assembly 112 comprises a fitting 152 and a plano-convex lens 156 with a convex side 160 toward cable 148 and a plane side 164 toward reflecting end 128 of plug 108. First fiber optic cable 148 is positioned in the focal plane A of lens 156, but just to the side of its optic axis B which is perpendicular to reflecting end 128 of plug 108. Light from first optic cable 148 is collimated by lens 156 but emerges at a slight angle from the normal. This off-axis collimated light travels through the sample between plane side 164 and relecting end 128 of plug 108 which reflects it back through the sample to lens 156. The light beam is still collimated but is returning at an angle to the optic axis B of lens 156 that is the negative of the incident angle of the light beam which left lens 156. Lens 156 directs the light beam to a spot on the focal plane where a second fiber optic cable 168 conducts the light to a remote detector (not shown) for spectrophotometric analysis A control fluid, introduced behind plug 108 via bottom port 116, moves plug 108 close to lens assembly 112 so that plug 108 displaces the sample fluid which is expelled from probe body 104 via exit 124. The control fluid may be the sample fluid itself, air or some other suitable fluid.

A comparison of FIGS. 1 and 2 show the probe in the reference position and sampling position, respectively. As shown in FIG, 1, when a control fluid, which may be the sample fluid or may be another fluid such as water or air, is flowing through bottom port 116 into probe body 104, plug 108 is driven against lens assembly 112. A reference intensity spectrum is measured. This spectrum is characteristic of the apparatus and is used to produce, conduct and measure the light intensity as well as any small amount of sample between plug 108 and lens assembly 112.

When control fluid flow is interrupted, plug 108 may fall back into its test position at the bottom of probe body 104 if probe 100 is oriented with lens assembly 112 up and bottom port 116 down. The influx of fluid sample at inlet 120 could also push plug 108 away from lens assembly 112. When control fluid is stopped from entering bottom port 116 by a conventional valving arrangement (not shown), sample fluid can enter inlet 120 as plug 108 slides toward bottom port 116 so that a second light intensity spectrum is collected. The ratio of the test light intensity spectrum to the reference light intensity spectrum is the transmission spectrum of the sample fluid which flowed into probe body 104 when plug 108 settled to the bottom of probe body 104.

Probe 100 can be constructed from stainless steel compression fittings and connectors. Plug 108 is preferably made of polished stainless steel rod having a longitudinal groove 132 machined therein and plug body 104 has a matching pin 140 to restrict the rotation of the reflecting end 128 and to help keep plug 108 aligned with lens 156.

The control fluid is preferably compressed air capable of providing a flow rate of about 0.5 standard cc/min flow to move the reflecting plug 108. Test spectra can be collected approximately 8 seconds after reference spectra by allowing the reflecting plug 108 to return to the sampling position by interrupting the fluid flow to bottom port 116. A probe constructed according to the present invention can produce measurement having deviations of less that +/−0.15% and RMS deviation of less than 0.0025%. Without groove 132 and pin 140, a probe constructed otherwise in accordance with the present invention produces measurements having deviations less than 1.5% and RMS deviation of less than 0.3%.

The foregoing description of preferred embodiments of the invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use comtemplated. It is intended that the scope of the invention be defined by the claims appended hereto.

What is claimed is:

1. A spectrometric probe use with a source of light and a detector for making spectrophotometric measurements of a fluid sample, said probe comprising:
    a hollow probe body having an interior;
    a plug slidably positioned in said probe body, said plug having a reflective surface;
    lens means for directing light onto said reflective surface of said plug and receiving light reflected by said reflective surface, said lens means within said probe body,
    said plug able to slide to a reference position a first distance with respect to said lens means and to a sampling position a second distance from said lens means ; and
    valve means for admitting fluid sample into and expelling fluid sample from the interior of said hollow probe between said plug and said lens means said fluid sliding said plug to said sampling position when said fluid is admitted to the interior of said hollow probe.

2. The probe as recited in claim 1, further comprising means for guiding said plug between said reference position and said sampling position.

3. The probe as recited in claim 2, wherein said guiding means is a pin in said probe body and a slot in said plug, said pin riding in said slot as said plug moves between said reference and said sampling position.

4. The probe as recited in claim 2, wherein said guiding means is a slot in said probe body and a pin in said plug, said pin traveling in said slot as said plug moves between said reference and said sampling position.

5. The probe as recited in claim 1, further comprising means for carrying light from said light source to said probe body and from said probe body to said detector.

6. The probe as recited in claim 2, further comprising means for carrying light from said light source to said probe body and from said probe body to said detector.

7. The probe as recited in claim 3, further comprising means for carrying light from said light source to said probe body and from said probe body to said detector.

8. The probe as recited in claim 4, further comprising means for carrying light from said light source to said probe body and from said probe body to said detector.

9. The probe as recited in claim 1, wherein said lens means is a planoconvex lens.

10. The probe as recited in claim 2, wherein said lens means is a planoconvex lens.

11. The probe as recited in claim 3, wherein said lens means is a planoconvex lens.

12. The probe as recited in claim 4, wherein said lens means is a planoconvex lens.

13. A spectrometric analyzer system for making spectrophotometric measurements of a fluid sample, said system comprising:
    a source of light;
    detector means for analyzing the spectrum of light received by said detector means;
    a hollow probe body having an interior;
    a plug slidably positioned in said probe body, said plug having a reflective surface;
    lens means for directing light onto said relective surface of said plug and receiving light reflected by said reflective surface, said lens means positioned within said probe body,
    said plug able to slide to a reference position at a first distance with respect to said lens means and to a sampling position at a second distance from said lens means;
    light guiding means for carrying light between said light source and said probe body and said probe body and said detector; and
    valve means for admitting said fluid sample to and expelling said fluid sample from the interior of said hollow probe between said plug and said lens means said fluid sliding said plug to said sampling position when said fluid is admitted to the interior of said hollow probe.

14. The analyzer system as recited in claim 13, further comprising means for guiding said plug between said reference position and said sampling position.

15. The analyzer system as recited in claim 14, wherein said guiding means is a pin in said probe body and a slot in said plug, said pin riding in said slot as said plug moves between said reference and said sampling position.

16. The analyzer system as recited in claim 14, wherein said guiding means is a slot in said probe body and a pin in said plug, said pin traveling in said slot as said plug moves between said reference and said sampling position.

17. The analyzer system as recited in claim 13, further comprising means for carrying light from said light source to said probe body and from said probe body to said detector.

18. The analyzer system as recited in claim 13, wherein said lens means is a planoconvex lens.

19. A method for making spectrophotometric measurements of a fluid sample using a source of light, detector means for spectrally analyzing light and a reflector, said light source and said reflector in spaced relation, said method comprising the steps of:
    directing said light through said sample to said reflector so that said light is reflected to said detector means;
    making a first spectral measurement;
    moving said light source and said reflector relative to each other by pressure of said fluid;
    making a second spectral measurement; and
    comapring said first and second spectral measurements.

* * * * *